(12) United States Patent
Wieters

(10) Patent No.: US 10,932,655 B2
(45) Date of Patent: Mar. 2, 2021

(54) ELECTROMAGNETIC ACTUATOR FOR A SURGICAL INSTRUMENT AND METHOD FOR PRODUCING SAME

(71) Applicant: OLYMPUS WINTER & IBE GMBH, Hamburg (DE)

(72) Inventor: Martin Wieters, Barsbuettel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 16/570,101

(22) Filed: Sep. 13, 2019

(65) Prior Publication Data
US 2020/0000324 A1    Jan. 2, 2020

Related U.S. Application Data

(63) Continuation of application No. PCT/EP2018/057317, filed on Mar. 22, 2018.

(30) Foreign Application Priority Data

Apr. 6, 2017 (DE) ..................... 10 2017 107 397.3

(51) Int. Cl.
*H02K 33/16* (2006.01)
*A61B 1/00* (2006.01)
(Continued)

(52) U.S. Cl.
CPC ....... *A61B 1/00158* (2013.01); *H02K 41/031* (2013.01); *A61B 2017/00398* (2013.01);
(Continued)

(58) Field of Classification Search
CPC .... H02K 33/16; H02K 41/031; H01F 7/1615; H01F 7/122
See application file for complete search history.

(56) References Cited

U.S. PATENT DOCUMENTS 3,248,499 A * 4/1966 Young ................... H01F 7/1646
335/81
4,000,481 A * 12/1976 Pang ..................... H01F 7/1615
335/170
(Continued)

FOREIGN PATENT DOCUMENTS

DE   10 2014 204 736 A1   9/2015
WO      2013/000429 A1   1/2013

OTHER PUBLICATIONS

International Search Report dated Jun. 6, 2018 received in PCT/EP2018/057317.

*Primary Examiner* — Dang D Le
(74) *Attorney, Agent, or Firm* — Scully, Scott, Murphy & Presser, P.C.

(57) ABSTRACT

An electromagnetic actuator for use with a surgical instrument. The electromagnetic actuator including: a stator arranged outside a tube; and a rotor mounted in the tube such that the rotor can move in the tube in a longitudinal axial direction of the tube; the rotor includes one or more of a paramagnetic and ferromagnetic material and is movable in the longitudinal axial direction by application of an electromagnetic field; the stator includes: a distal permanent magnet and a proximal permanent magnet, the distal permanent magnet and the proximal permanent magnet being oppositely polarized in the longitudinal axial direction; and at least one electric coil for generating the electromagnetic field; wherein the distal permanent magnet and the proximal permanent magnet are arranged on an outer side of the coil facing away from the tube.

12 Claims, 9 Drawing Sheets

(51) Int. Cl.
*H02K 41/03* (2006.01)
*A61B 34/00* (2016.01)
*A61B 17/00* (2006.01)
*H01F 5/00* (2006.01)

(52) U.S. Cl.
CPC ............. *A61B 2017/00876* (2013.01); *A61B 2034/731* (2016.02); *H01F 5/00* (2013.01)

(56) References Cited

U.S. PATENT DOCUMENTS

| | | | | |
|---|---|---|---|---|
| 4,315,197 | A * | 2/1982 | Studer | H02K 35/06 |
| | | | | 310/12.12 |
| 5,896,076 | A | 4/1999 | van Namen | |
| 7,382,067 | B2 * | 6/2008 | Nakagawa | H01F 7/1615 |
| | | | | 310/15 |
| 7,605,680 | B2 * | 10/2009 | Matsumoto | H01F 7/081 |
| | | | | 335/103 |
| 7,800,470 | B2 * | 9/2010 | Wright | F16K 31/0679 |
| | | | | 335/229 |
| 8,084,898 | B2 * | 12/2011 | Kawano | A61B 34/72 |
| | | | | 310/12.14 |
| 8,449,274 | B1 * | 5/2013 | Zelechonok | F04B 17/04 |
| | | | | 417/417 |
| 2006/0176589 | A1 | 8/2006 | Shu et al. | |
| 2013/0314517 | A1 | 11/2013 | Makiyama et al. | |
| 2017/0005557 | A1 | 1/2017 | Wieters | |

* cited by examiner

Fig. 2
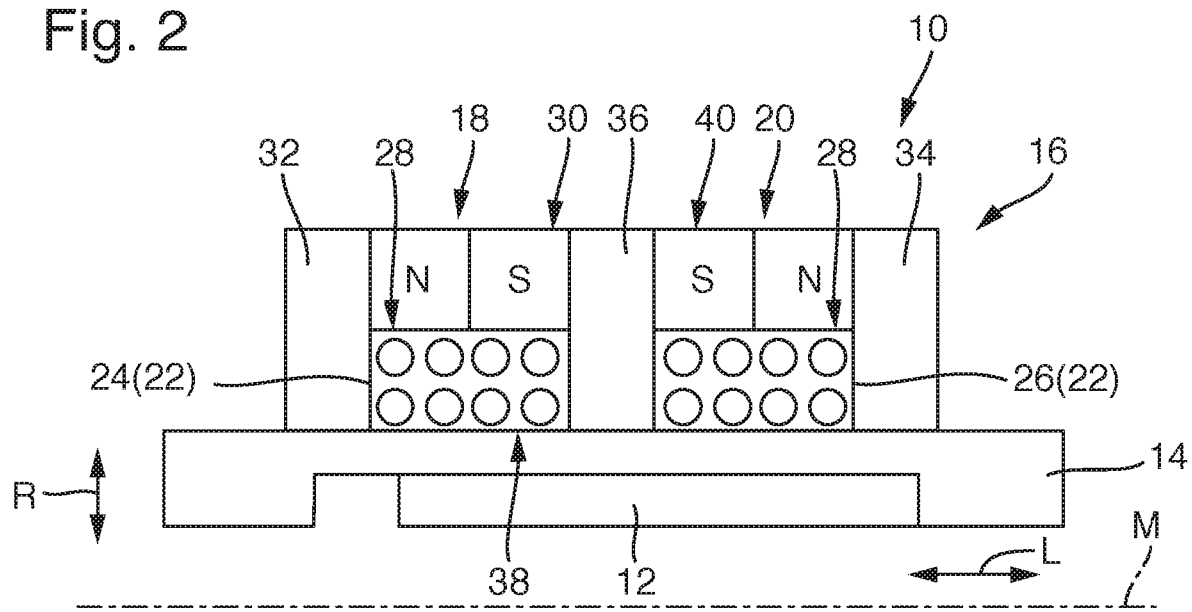
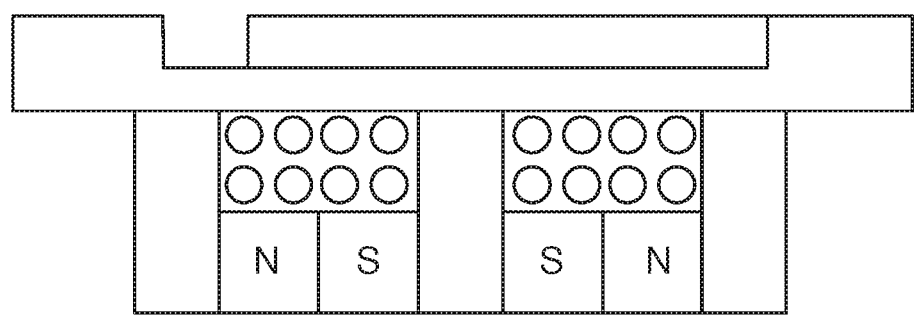

ELECTROMAGNETIC ACTUATOR FOR A SURGICAL INSTRUMENT AND METHOD FOR PRODUCING SAME

CROSS-REFERENCE TO RELATED APPLICATION

The present application is a continuation of PCT/EP2018/057317 filed on Mar. 22, 2018, which is based upon and claims the benefit to DE 10 2017 107 397.3 filed on Apr. 6, 2017, the entire contents of each of which are incorporated herein by reference.

BACKGROUND

Field

The present disclosure relates to an electromagnetic actuator for a surgical instrument, comprising a stator arranged outside a tube and a rotor mounted in the tube such that it can move in the tube in a longitudinal axial direction of the tube, wherein the rotor at least partially comprises a paramagnetic and/or ferromagnetic material and can be moved in the longitudinal axial direction by application of an electromagnetic field, wherein the stator comprises a distal permanent magnet and a proximal permanent magnet that are oppositely polarized in the longitudinal axial direction, and at least one electric coil for generating the electromagnetic field. The present disclosure further relates to a surgical instrument having such an electromagnetic actuator. Finally, the present disclosure relates to a method for producing an electromagnetic actuator for a surgical instrument, comprising a stator arranged outside a tube and a rotor mounted in the tube such that it can move in the tube in a longitudinal axial direction of the tube, wherein the rotor at least partially comprises a paramagnetic and/or ferromagnetic material and can be moved in the longitudinal axial direction by application of an electromagnetic field, wherein the stator comprises a distal permanent magnet and a proximal permanent magnet that are oppositely polarized in the longitudinal axial direction, and at least one electric coil for generating the electromagnetic field.

Prior Art

Electromagnetic actuators have many and varied applications. For example, switches can be operated, or micro-optics set or adjusted, with them. In the case of surgical instruments, for example endoscopes, these compact-design actuators can be used in order to alter a focus or a magnification of an optical system. In the case of endoscopes having a variable viewing direction, it is in addition possible to set or alter a viewing direction of the optical system with the aid of an electromagnetic actuator. The optical characteristics of an optical system are altered by moving an optical component, for example a lens, a prism or an aperture by means of the actuator, wherein the optical component is located in or on the rotor of the actuator.

Bistable and monostable electromagnetic actuators are known. In the case of a bistable electromagnetic actuator, a rotor is provided, which is held in a permanent magnetic field in one of two extreme positions (end positions) and, by switching an electromagnetic field, can be transferred from one of these two stable positions into the other stable position respectively. In the case of a monostable electromagnetic actuator, the rotor is held stably in its resting position by a magnetic field which is generated by one or more permanent magnets. As a result of applying an electromagnetic field generated by a magnetic coil, the rotor is moved out of said stable resting position. Bistable systems are suitable for two-stage operation with end positions which are maintained without power. On the other hand, monostable systems are suitable for continual adjustment.

A bistable electromagnetic actuator is known, for example, from DE 10 2014 204 736 A1. In the case of this electromagnetic actuator, coils, yokes and magnets are arranged next to one another in the stator, wherein the coils and the yokes are arranged in a longitudinal axial direction between two oppositely polarized magnets. In addition, a return element is provided which, like the rotor, is produced from a ferromagnetic material. The rotor and the stator are separated from one another by a sliding tube. The stator sits on the outside diameter of the sliding tube and the rotor slides on the inner side of the sliding tube into the inside diameter thereof.

These conventional systems have a relatively large stator in a longitudinal axial direction, in which the rotor moves and, as a consequence, also have a relatively large overall size. This restricts the possibilities of deploying such drives in an undesirable manner.

SUMMARY

It is an object to provide an electromagnetic actuator, a surgical instrument having an electromagnetic actuator, as well as a method for producing an electromagnetic actuator, wherein the electromagnetic actuator is to have a compact overall size.

Such object can be achieved by an electromagnetic actuator for a surgical instrument, comprising a stator arranged outside a tube and a rotor mounted in the tube such that it can move in the tube in a longitudinal axial direction of the tube, wherein the rotor at least partially comprises a paramagnetic and/or ferromagnetic material and can be moved in the longitudinal axial direction by application of an electromagnetic field, wherein the stator comprises a distal permanent magnet and a proximal permanent magnet that are oppositely polarized in the longitudinal axial direction, and at least one electric coil for generating the electromagnetic field, wherein the permanent magnets can be arranged on an outer side of the coil, facing away from the tube.

Due to at least such arrangement of the permanent magnets on the outer side of the coils, the system can be compact in the longitudinal axial direction. Such a compact system can be used in surgical instruments such as, for example, endoscopes, additionally for example endoscopes having a flexible, semi-flexible or rigid shaft.

The distal and the proximal permanent magnets can form a magnetic return element for the magnetic field generated by the electric coil. The magnetic return can be effected in the case of such an electromagnetic actuator via the permanent magnets themselves. As a result, it is possible to save on the otherwise standard magnetic return element. The installation space required for the electromagnetic actuator can be consequently smaller.

According to a further embodiment, an outer side of the permanent magnets facing away from the tube can form at least one partial surface of an outer side of the stator facing away from the tube. In other words, the electromagnetic actuator according to this embodiment does not comprise a magnetic return element which is traditionally arranged on the outer side of the actuator facing away from the tube. Said construction can provide a compact design of the electromagnetic actuator, such as a small diameter of the system.

It is additionally provided that a distal end of the stator can be formed by a distal stator pole shoe and an opposite proximal end in the longitudinal axial direction can be formed by a proximal stator pole shoe. Using stator pole shoes can increase the efficiency of the electromagnetic actuator. As a result, larger retention forces can be provided or lower control currents can be deployed.

In an embodiment, the stator can comprise a central stator pole shoe which is arranged between the permanent magnets in the longitudinal axial direction. Due to such configuration of the central stator pole shoe, the efficiency of the magnetic system can be further improved. The use of a central stator pole shoe can be used in a bistable system. In the central stator pole shoe, the magnetic flows generated by the oppositely polarized permanent magnets are guided from the region of the rotor back in the direction of the permanent magnets.

The central stator pole shoe can be thicker than the outer stator pole shoe(s), i.e. the distal stator pole shoe or the proximal stator pole shoe. For example, the central stator pole shoe can have a material thickness, measured in the longitudinal axial direction, which is 1.2-times to double the size of the material thickness of the outer pole shoes measured in the same direction. Furthermore, the distal stator pole shoe and the proximal stator pole shoe can have the same material thickness, measured again in the longitudinal axial direction.

According to a further embodiment, the central stator pole shoe can extend in a radial direction perpendicular to the longitudinal axial direction from the inner side of the coil facing the tube up to the outer side of the permanent magnets facing away from the tube and the coil can comprise a distal coil and a proximal coil, wherein the distal and proximal coils can extend in the longitudinal axial direction on both sides of the central stator pole shoe and are electrically connected to one another such that the distal coil generates a first magnetic field which is oriented identically to a second magnetic field generated by the proximal coil.

In other words, the first magnetic field and the second magnetic field can be oriented in a same direction. The dimensioning of the pole shoes allows for an efficient flow guidance and, as a result, further increases the efficiency of the electromagnetic actuator.

It is additionally provided that the central stator pole shoe can be formed from a proximal central stator part pole shoe and from a distal central stator part pole shoe. Such a construction allows the formation of a distal assembly and a proximal assembly. The use of assemblies can simplify and accelerate production of the electromagnetic actuator.

According to a further embodiment, an air gap can be provided between the distal central stator part pole shoe and the proximal central stator part pole shoe. In other words, the distal and the proximal assembly do not need to be mechanically connected to one another. Since the permanent magnets of the two assemblies repel one another, the two assemblies can be aligned autonomously and independently of any existing component tolerances with a distal and a proximal stop.

According to an alternative embodiment and in the event that a mechanical connection of the two assemblies is desired, an adhesive can be provided between the assemblies, which does not show any volume shrinkage or only shows a low volume shrinkage during curing. For example, an adhesive which loses less than 5% volume during curing can be used.

According to an embodiment, the distal stator pole shoe, the distal coil, the distal permanent magnet and the distal central stator part pole shoe can form a prefabricated distal assembly and the proximal central stator part pole shoe, the proximal coil, the proximal permanent magnet and the proximal stator pole shoe can form a prefabricated proximal assembly, wherein the components of the distal and/or the proximal assembly can be bonded to one another.

It is additionally provided that the distal assembly and the proximal assembly can have an identical construction to one another. In order to realize the opposite magnetic orientation of the permanent magnets in the electromagnetic actuator, it is provided that either the proximal assembly or the distal assembly can be installed, rotated by 180° with respect to the other assembly in each case during erection. It should additionally be observed, in connection with this, that the magnetic coils provided in the assemblies can be wired appropriately so that they generate magnetic fields having the same orientation.

Using assemblies accelerates the production of the electromagnetic actuator. Thus, according to a further embodiment, the assemblies can be prefabricated structural elements.

According to a further embodiment, at least one of the stator pole shoes can extend in a radial direction perpendicular to the longitudinal axial direction from an inner side of the coil facing the tube up to an outer side of the permanent magnets facing away from the tube. Furthermore, all of the stator pole shoes can extend in a radial direction from the outer side of the tube, which rests on the inner side of the coil and therefore define the same dimension, up to an outer side of the permanent magnets facing away from the tube. This dimensioning of the stator pole shoes can allow an efficient flow guidance of the magnetic field.

It is additionally provided that the permanent magnets can be annular magnets which enclose the coils. According to an alternative embodiment, the distal and the proximal permanent magnet can each be formed from at least one bar magnet.

The use of bar magnets can provide a reduction in the installation space taken up by the electromagnetic actuator. The rotor and coil can be executed with a constant cross-section and the magnets arranged thereover, that is to say radially further outwardly, no longer require any circumferential installation space. It is thus possible for further structural elements of the endoscope to be accommodated in the installation space which thus becomes available, such as where the electromagnetic actuator is inserted in an endoscope shaft. Bar magnets are additionally mechanically significantly more stable than magnet rings which, due to their design, have to have a very small wall thickness. The handling of the bar magnets is therefore considerably simpler than that of magnet rings, which simplifies and accelerates the production of the electromagnetic actuator.

It is additionally provided that the distal and the proximal permanent magnet can each be formed from multiple bar magnets, wherein the bar magnets forming the distal and/or the proximal permanent magnets can be arranged uniformly spaced along the circumference of the tube. Due to the use of a plurality of bar magnets, the provided magnetic force can be increased since a larger magnetic flow can be generated by multiple magnets. A homogeneous magnetic field can be generated by the uniform spacing of the bar magnets.

According to a further embodiment, at least one of the permanent magnets can comprise magnetically hard particles which are embedded in a plastic matrix, wherein said permanent magnet can be produced using an injection molding method. For example, NdFeB particles (neodymium, iron, boron) or a mixture of particles of said materials, which are for example stirred into an epoxy resin adhesive, is/are suitable as magnetic particles. In order to produce the permanent magnets, a cavity between the stator pole shoes is for example emptied, which is to be occupied by the permanent magnets. Such configuration can be used where the electromagnetic actuator comprises a prefabricated distal and proximal assembly. During the production of the assemblies, not only can the magnetic material be introduced in this way, but the fixing of the stator pole shoes and of the coil can also be prepared or respectively performed in the same step. Additionally, the entire assembly can be subsequently magnetized such that the magnetic particles assume a desired magnetic orientation.

According to a further embodiment, at least one coil wire of the coil can be molded in at least one permanent magnet. In other words, the supply cables of the coil can be guided through the permanent magnet. Thus, the installation space which would otherwise be required for the supply cables of the magnetic coils can be saved.

It is additionally provided that the rotor can have a total length in the longitudinal axial direction which is smaller than a maximum extent of the stator in this direction. By such a dimensioning of the stator and the rotor, a bistable electromagnetic actuator can be indicated. It is likewise possible to find other designs in which the electromagnetic actuator is bistable. In connection with this, the design and size of the permanent magnets and of the coils, for example, are of importance. According to a further embodiment, the rotor can have a larger extent than the stator in the longitudinal axial direction. A monostable actuator can be realized by configuring the electromagnetic actuator in such a way.

Such object is additionally achieved by a surgical instrument, such as an endoscope, having an electromagnetic actuator according to one or more of the embodiments indicated above.

The same or similar advantages apply to the surgical instrument as have already been mentioned with respect to the electromagnetic actuator, so that repetitions shall be dispensed with.

In addition, such object is achieved by a method for producing an electromagnetic actuator for a surgical instrument, comprising a stator arranged outside a tube and a rotor mounted in the tube such that it can move in the tube in a longitudinal axial direction of the tube, wherein the rotor at least partially comprises a paramagnetic and/or ferromagnetic material and can be moved in the longitudinal axial direction by application of an electromagnetic field, wherein the stator comprises a distal permanent magnet and a proximal permanent magnet that are oppositely polarized in the longitudinal axial direction, and at least one electric coil for generating the electromagnetic field, wherein the permanent magnets can be arranged on an outer side of the coil, facing away from the tube.

The same or similar advantages also apply to the method for producing an electromagnetic actuator as have already been mentioned with respect to the electromagnetic actuator.

According to an embodiment, the permanent magnets can be arranged in such a manner that an outer side of the permanent magnets facing away from the tube forms at least one partial surface of an outer side of the stator facing away from the tube. In other words, no magnetic return element, such as no magnetic return element which is provided on the outer side of the stator, is necessary during the method for producing the electromagnetic actuator.

It is additionally provided that a distal stator pole shoe can be arranged distally to the distal permanent magnet and can form a distal end of the stator and a proximal stator pole shoe is arranged proximally to the proximal permanent magnet and can form an opposite proximal end in the longitudinal axial direction. It is additionally provided that a central stator pole shoe can be arranged between the permanent magnets in the longitudinal axial direction.

According to a further embodiment, the central stator pole shoe can extend in a radial direction perpendicular to the longitudinal axial direction from the inner side of the coil facing the tube up to the outer side of the permanent magnets facing away from the tube and the coil can comprise a distal coil and a proximal coil, wherein the distal stator pole shoe, the distal coil, the distal permanent magnet and the distal central stator part pole shoe can be joined to form a prefabricated distal assembly and the proximal central stator part pole shoe, the proximal coil, the proximal permanent magnet and the proximal stator pole shoe can be joined to form a prefabricated proximal assembly, wherein the components of the distal and/or the proximal assembly can be bonded to one another, and the prefabricated proximal assembly and the prefabricated distal assembly can be subsequently mounted, wherein the two coils are electrically connected to one another such that the distal coil generates a first magnetic field which can be oriented identically to a second magnetic field generated by the proximal coil and the central stator pole shoe can be formed from the proximal central stator part pole shoe and from the distal central stator part pole shoe.

The use of two assemblies can provide a more rapid and more efficient mounting possible. At the same time, the alignment/adjustment of the proximal stator pole shoe with/ to the proximal stop and also the alignment/adjustment of the distal stator pole shoe with/to the distal stop can be simpler and considerably more precise. The alignment of the stator pole shoes with the stops can provide for the correct function of the electromagnetic actuator. The distal side of the stator pole shoe can lie on the distal edge of the rotor, that is to say on the distal stop. The same can apply to the alignment of the proximal stator pole shoe and of the proximal stop. The distal and proximal stator pole shoes can be conventionally aligned independently of one another with the stops of the rotor. The proximal pole shoe can be aligned with the proximal stop. The distal stator pole shoe can be aligned by means of the components of the stator, inasmuch as this is possible within the framework of the component tolerances. During this process, the production tolerances of the components are added up. This has a correspondingly negative effect on the positioning of the distal component. The same of course also applies to the positioning of the proximal component.

During the use of two independent assemblies, wherein the assemblies have oppositely polarized permanent magnets to one another, the proximal and the distal stator pole shoe can be aligned independently of one another with the sliding tube or respectively with the stops. The units which are produced as finished assemblies prior to the final mounting can be installed opposite one another such that the permanent magnets repel one another. When the two assemblies are pushed together, a repelling force acts on the assemblies. The consequence of this is that the distal assembly moves in the direction of a distal stop and the proximal assembly moves in the direction of a proximal stop until the corresponding stop is reached. As a result, the two assemblies can be aligned in the desired position.

According to a further embodiment, an air gap can be provided between the assemblies, that is to say between the proximal central stator part pole shoe of the distal assembly and the distal central stator part pole shoe of the proximal assembly. The distal and the proximal assemblies are therefore not bonded or otherwise mechanically connected to one another. A constant property of adhesive is that its volume shrinks during curing, that is to say it occupies a smaller volume in the cured condition than in the uncured condition. This shrinkage effect would then, once again, impair the alignment of the two assemblies which has been solved with respect to one another. Consequently, dispensing with an adhesive between the two assemblies can avoid such problem.

It is additionally provided that in order to connect the two assemblies, an adhesive can be deployed, which can have a low volume shrinkage during the curing process. For example, adhesives are known which lose less than 5% of their volume during curing. Such an adhesive can be used for connecting the two assemblies.

According to a further embodiment, the first and/or the second assembly can be produced with a permanent magnet which can comprise magnetically hard particles which can be embedded in a plastic matrix, wherein said permanent magnet can be produced using an injection molding method and the plastic matrix can simultaneously serve as an adhesive for the components of the first and/or second assembly. Thus, both the permanent magnet is produced, and the components of the assemblies can be connected to one another, in one work step.

Using magnetically hard particles which are embedded in a plastic matrix in order to produce the permanent magnets can be used, since at least one coil wire of the coil is molded in at least one permanent magnet. It is thus possible to save on installation space for guiding through the connecting cables of the coils.

Further features will become evident from the description of embodiments, together with the claims and the appended drawings. Embodiments can fulfill individual features or a combination of several features.

BRIEF DESCRIPTION OF THE DRAWINGS

The embodiments are described below without limiting the general concept of the invention by means of exemplary embodiments with reference to the drawings, wherein reference is expressly made to the drawings regarding all of the details which are not explained in greater detail in the text, wherein:

FIG. 2 illustrates an electromagnetic actuator in a deenergized condition, the rotor of which is located in an end position, in a schematically simplified longitudinal sectional view.

In the drawings, the same or similar elements and/or parts are, in each case, provided with the same reference numerals so that they are not introduced again in each case.

DETAILED DESCRIPTION

Figure 1:
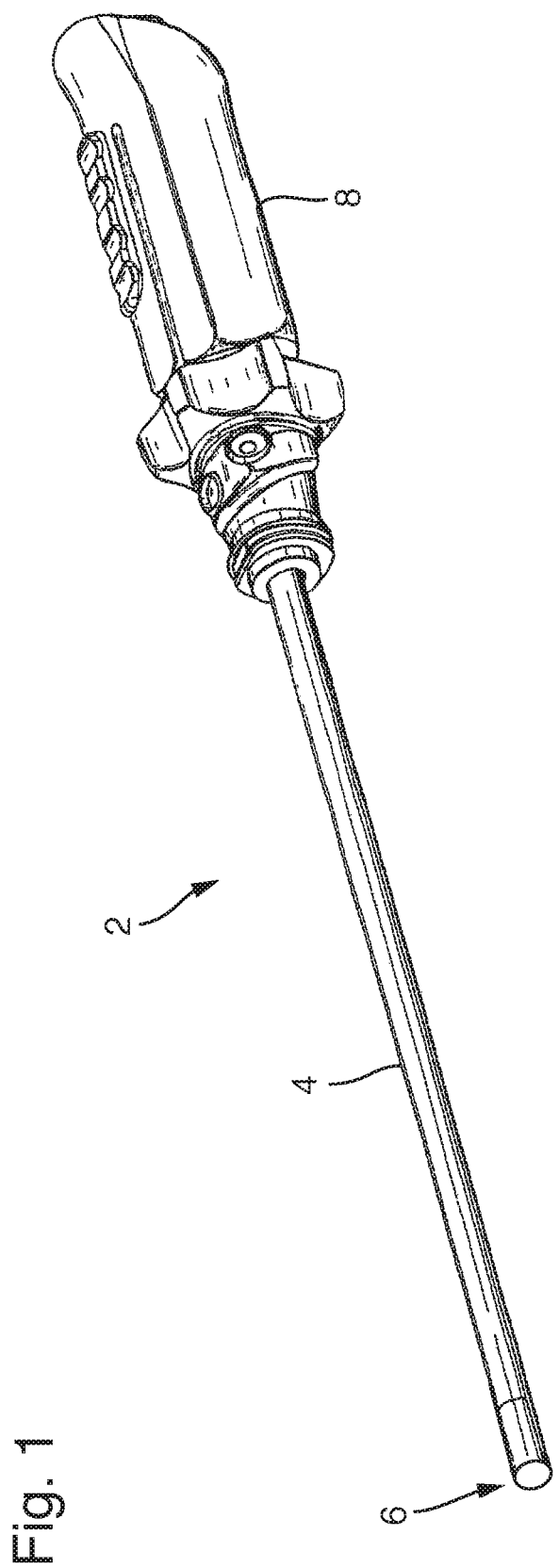
FIG. 1 illustrates an endoscope as an exemplary surgical instrument in a schematically simplified perspective view.

FIG. 1 shows an endoscope 2 as an exemplary surgical instrument in a schematically simplified perspective view. The endoscope 2 comprises an endoscope shaft (or insertion section) 4, in which an optical system is arranged, with which an operation or observation field lying in front of a distal end 6 of the endoscope shaft 4 is imaged, for example, on an image sensor. A handle 8 is located on a proximal end of the endoscope 2. The optical system arranged in the endoscope shaft 4, which is not represented in FIG. 1, comprises an electromagnetic actuator.

FIG. 2 shows such an electromagnetic actuator 10 in a schematically simplified longitudinal sectional view. The electromagnetic actuator 10 is shown in a deenergized condition, in which the rotor thereof 12 is located in a proximal end position. The rotor 12 is received so that it can be moved within a tube 14 in a longitudinal axial direction L. A stator 16 of the electromagnetic actuator 10 is arranged outside the tube 14. The rotor 12 at least partially comprises a paramagnetic and/or ferromagnetic material. During application of an electromagnetic field to the rotor 12, the latter can be moved within the tube 14 in the longitudinal axial direction L.

The stator 16 comprises a distal permanent magnet 18 and a proximal permanent magnet 20. By way of example, these magnets 18, 20 are annular magnets. The magnets 18, 20 are polarized in the longitudinal axial direction L, i.e. their north-south direction lies at least approximately parallel to the longitudinal axial direction L. The distal permanent magnet 18 and the proximal permanent magnet 20 are arranged in the electromagnetic actuator 10 such that these are oppositely polarized. Additionally, at least one electric coil 22 is comprised, which serves to generate an electromagnetic field and, in the represented exemplary embodiment, is constructed from a distal coil 24 and a proximal coil 26. The permanent magnets 18, 20 are arranged on an outer side 28 of the coil 22, facing away from the tube 14.

Thanks to this arrangement, the distal permanent magnet 18 and the proximal permanent magnet 20 serve as a magnetic return element for the magnetic field generated by the electric coil 22. The permanent magnets 18, 20 form at least one partial surface of an outer side 30 of the stator 16 facing away from the tube 14.

The electromagnetic actuator shown in FIG. 2 is constructed rotationally symmetrical with respect to its central longitudinal axis M (represented in a dot-dashed manner). The indicated reference numerals are therefore exclusively cited in the upper part of the representation, but likewise apply to the corresponding components in the lower half.

The stator 16 comprises a distal stator pole shoe 32 at its distal end and a proximal stator pole shoe 34 at its opposite proximal end in the longitudinal axial direction L. Additionally, the stator 16 comprises a central stator pole shoe 36 which is arranged between the permanent magnets 18, 20 in the longitudinal axial direction L.

The central stator pole shoe 36, the distal stator pole shoe 32 and the proximal stator pole shoe 34 extend in a radial direction R perpendicular to the longitudinal axial direction L from an inner side 38 of the coil 22 facing the tube 14 up to an outer side 40 of the permanent magnets 18, 20 facing away from the tube 14.

Figure 3:
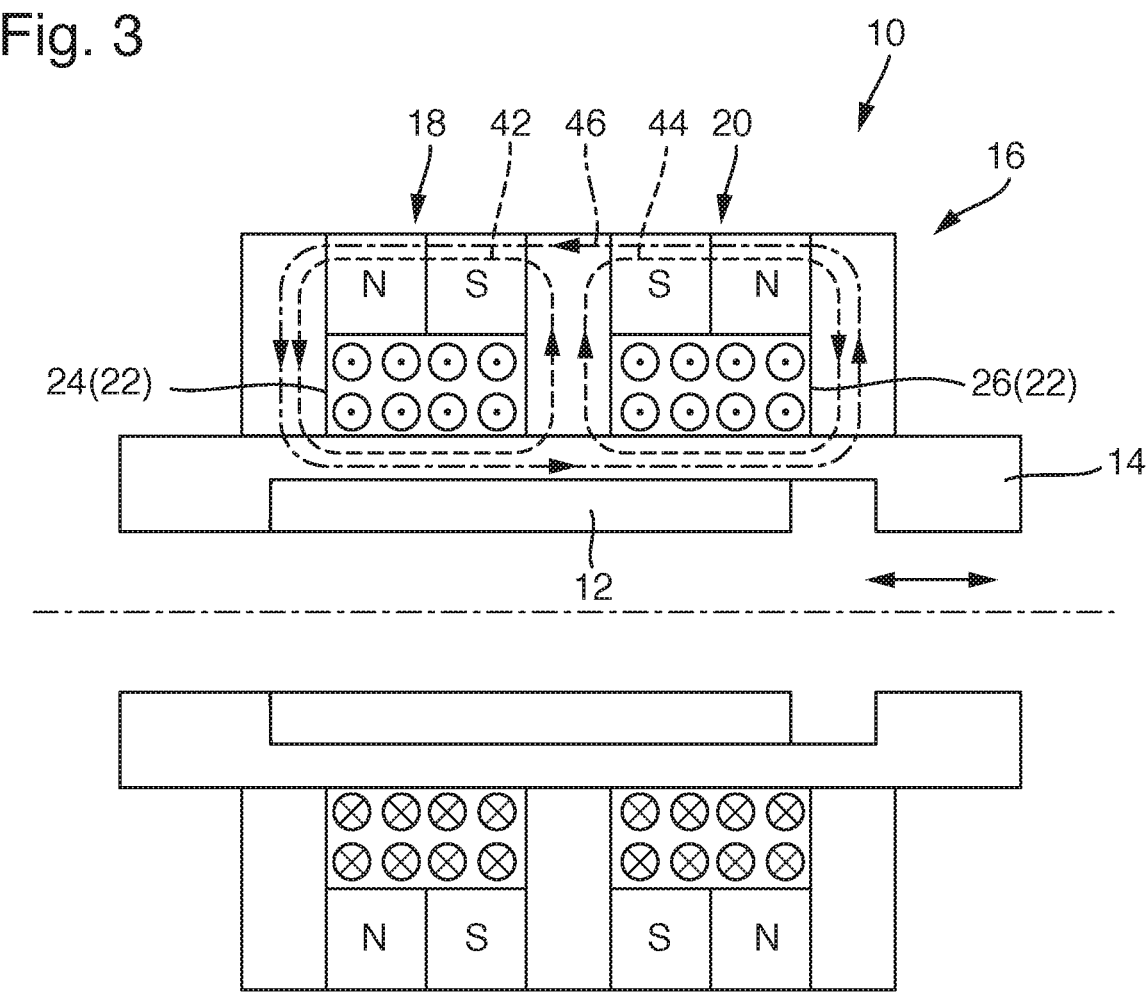
FIG. 3 illustrates the electromagnetic actuator in the energized condition, wherein the rotor thereof is located in the opposite end position, likewise in a schematically simplified longitudinal sectional view.

FIG. 3 likewise shows the electromagnetic actuator 10 of FIG. 2 in a schematically simplified longitudinal sectional view. The coil 22, i.e. the distal coil 24 and the proximal coil 26, is/are energized in the represented exemplary embodiment. The distal coil 24 and the proximal coil 26 are electrically coupled such that a first magnetic field generated by the respective coil 24, 26 and a second magnetic field are oriented in the same way. This is the result of the same energizing of the distal coil 24 and the proximal coil 26. The current flow direction is indicated in the schematically sketched conductors of the coils 24, 26. A current direction pointing out of the drawing plane is indicated by a dot and a current direction directed into the drawing plane is indicated by a cross. The first magnetic field and the second magnetic field add up to produce an electromagnetic field 46 of the coil 22.

The electromagnetic field 46 of the coil 22 superimposes a first static magnetic field 42 of the distal permanent magnet 18 and a second static magnetic field 44 of the proximal permanent magnet 20. At the distal end of the stator 16, the electromagnetic field 46 of the coil 22 and the first static magnetic field 42 of the distal permanent magnet 18 are constructively superimposed, while at the opposite proximal end of the stator 16 the magnetic field 46 of the coil 22 and the second static magnetic field 44 of the proximal permanent magnet 20 are destructively superimposed or respectively attenuated. If the rotor 12 is located in the position represented in FIG. 2, a force which displaces the rotor 12 into the position shown in FIG. 3 acts in the gap between the rotor 12 and the tube 14.

Figure 4:
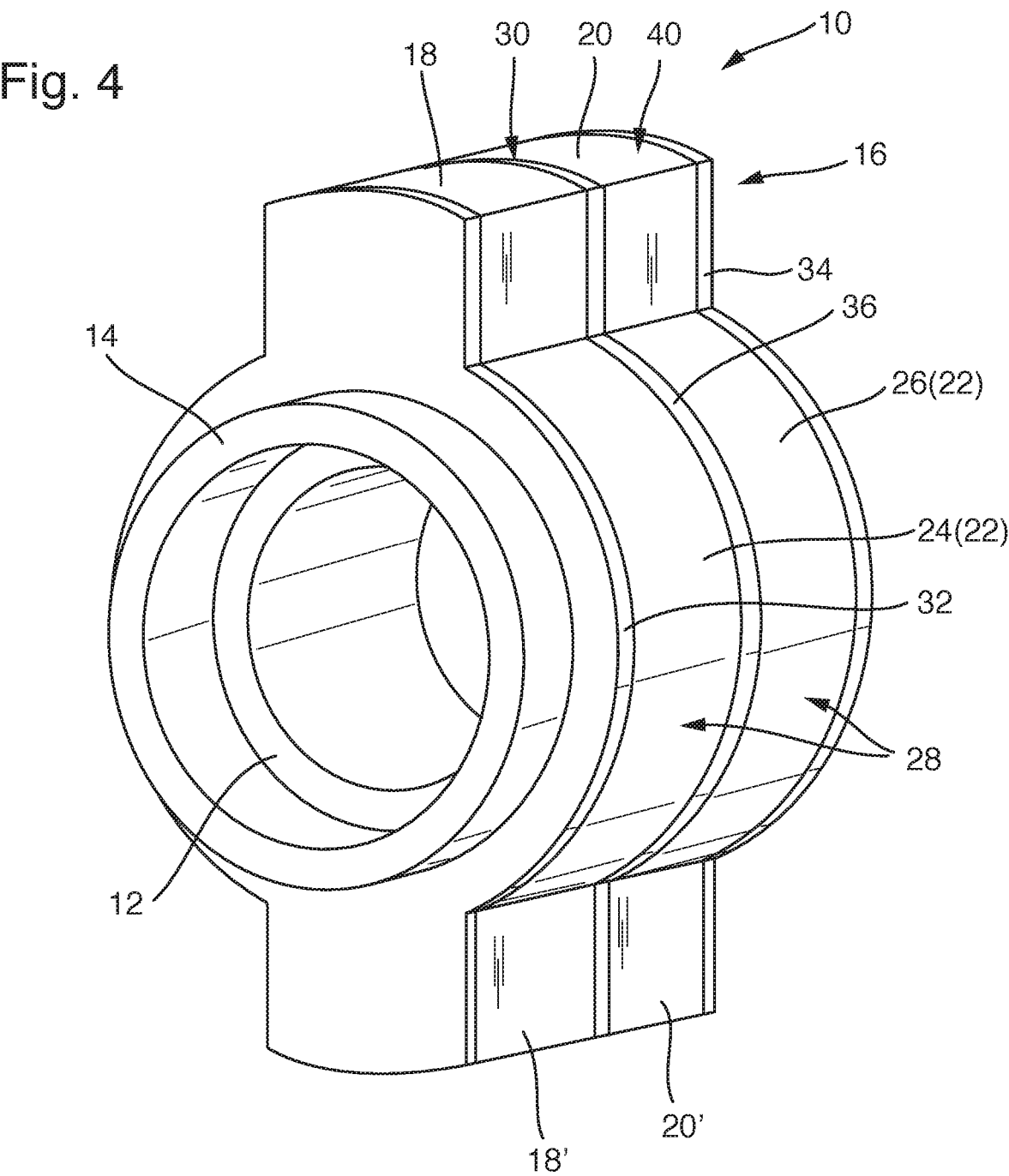
FIG. 4 illustrates a further electromagnetic actuator in a perspective schematically simplified representation.

FIG. 4 shows a further electromagnetic actuator 10 in a schematically simplified perspective representation. The distal permanent magnet 18 and the proximal permanent magnet 20 are executed as bar magnets or magnetic blocks in the represented exemplary embodiment. Both the distal permanent magnet 18 and the proximal permanent magnet 20 are constructed from multiple single magnets. For example, the distal permanent magnet comprises the components designated with reference numerals 18 and 18' and the proximal permanent magnet comprises the components designated with 20 and 20'. Said components are, for example, arranged uniformly spaced along the circumference of the tube 14. As an alternative to the bar magnets shown, annular permanent magnets can also be provided, which extend completely along the circumference on the outer side 28 of the coils 22.

Figure 5:
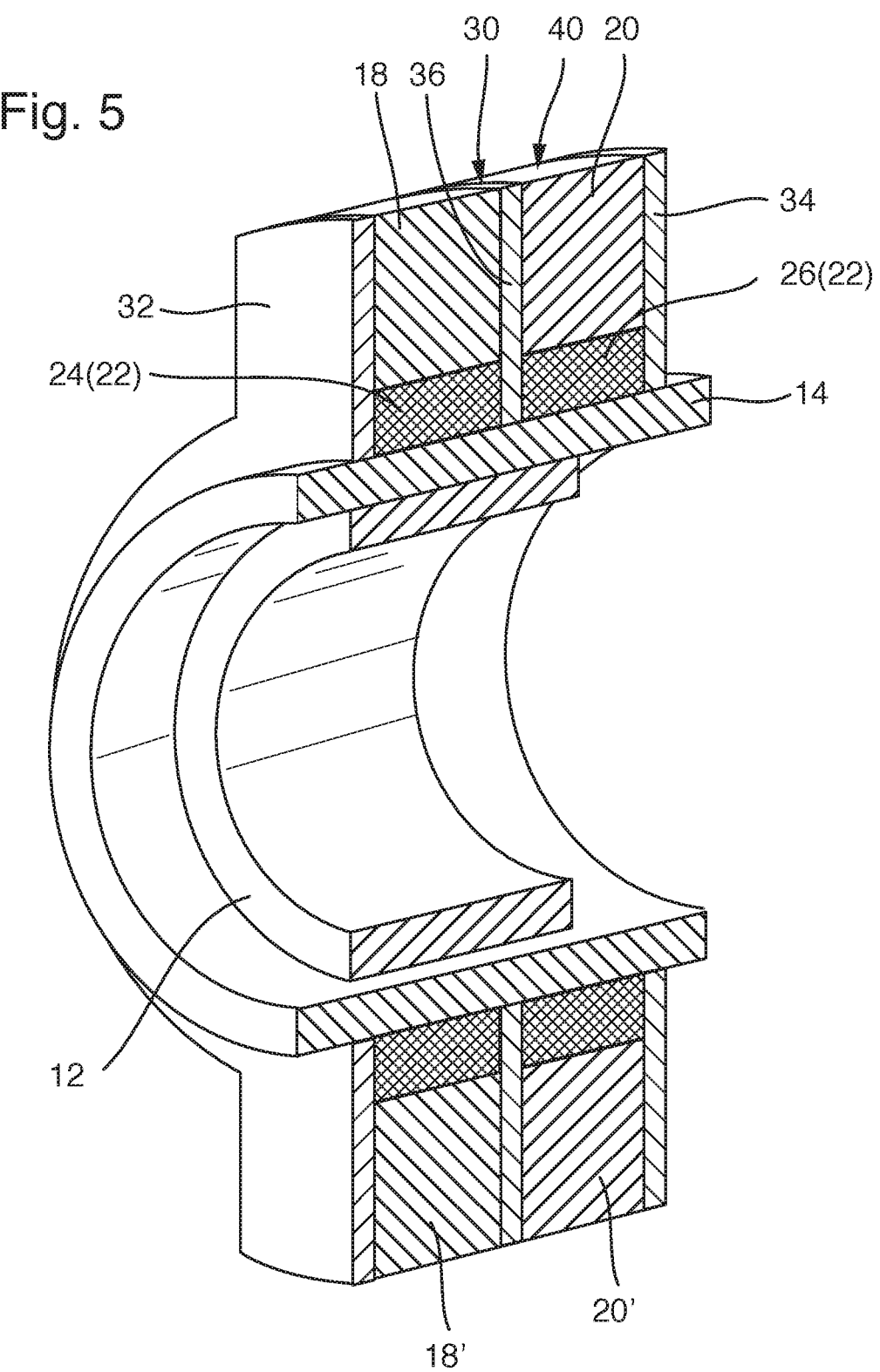
FIG. 5 illustrates the electromagnetic actuator in a schematically simplified sectioned perspective view which exposes the view of the interior of the actuator.

FIG. 5 shows the electromagnetic actuator 10 of FIG. 4, in a schematically simplified sectional view which exposes the view of the interior of the actuator. An optical element such as, for instance, a lens 62 or a prism, represented by way of example, of an optical system is received, for example, in the rotor 12. For example, the focus of an optical system can be altered with the aid of the electromagnetic actuator 10. Likewise, it is conceivable that the lens or group of lenses of such an optical system is/are adjusted with the aid of the electromagnetic actuator 10, for example in order to provide a zoom lens.

Figure 6:
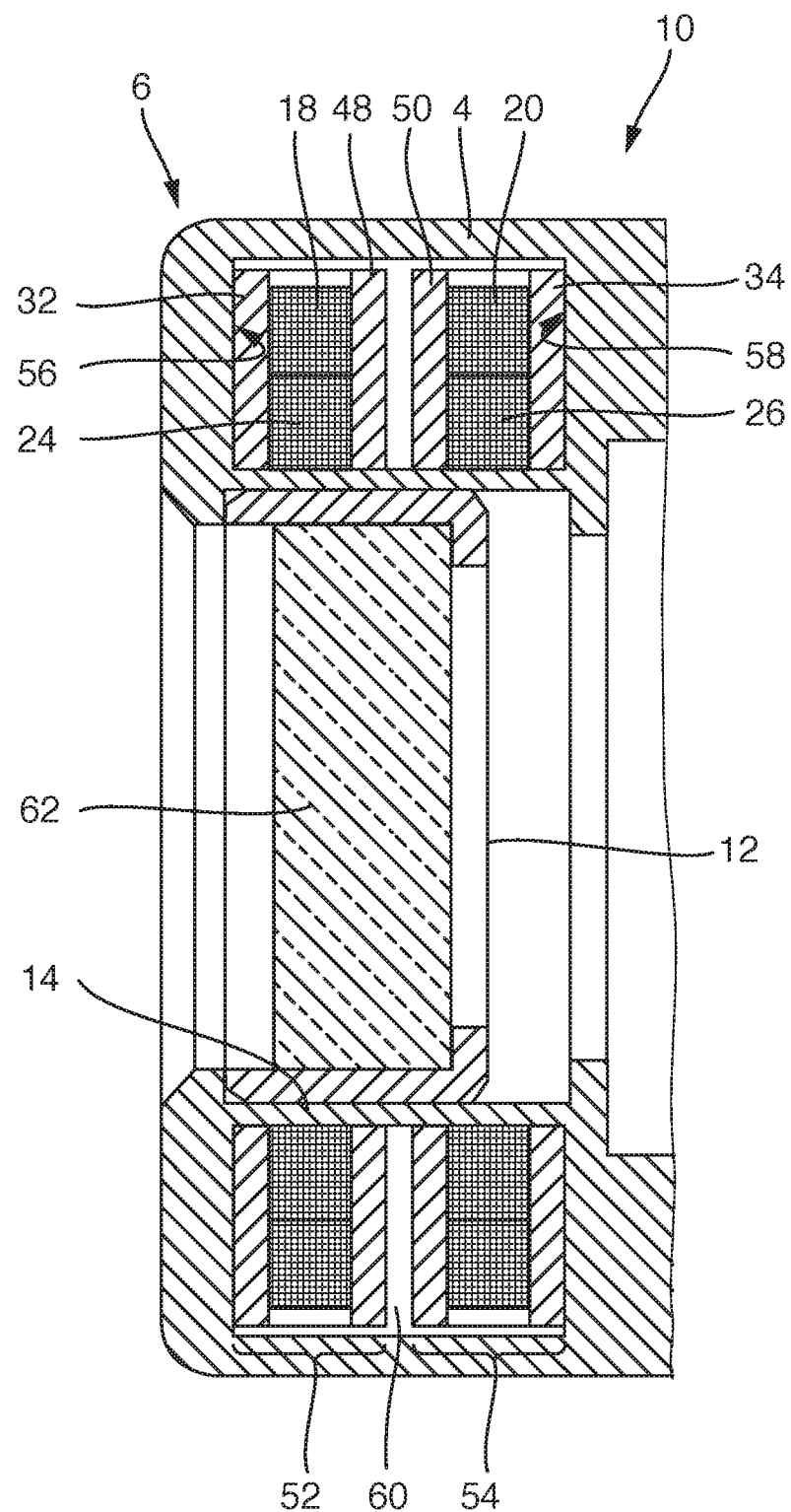
FIG. 6 illustrates a further electromagnetic actuator, constructed from a proximal and a distal assembly in the installed condition in an endoscope tube, in a schematically simplified longitudinal sectional view through the endoscope tube.

The central stator pole shoe 36 is, according to further exemplary embodiments, formed from a proximal central stator part pole shoe 50 and a distal central stator part pole shoe 48. FIG. 6 shows a corresponding electromagnetic actuator 10, in which this is realized. The electromagnetic actuator 10 is represented in an installed condition, it is located in an endoscope shaft 4 at a distal end 6 of the same.

The electromagnetic actuator 10 comprises a proximal assembly 54 and a distal assembly 52. The distal stator pole shoe 32, the distal coil 24, the distal permanent magnet 18 and the distal central stator part pole shoe 48 form the distal assembly 52. The proximal central stator part pole shoe 50, the proximal coil 26, the proximal permanent magnet 20 and the proximal stator pole shoe 34 form the proximal assembly 54. The assemblies 52, 54 are, for example, prefabricated components. In other words, these are joined together before they are brought together in the endoscope shaft 4 to form the shown arrangement. The components of the distal and/or the proximal assembly 52, 54 are additionally, for example, bonded to one another.

Since the permanent magnets 18, 20 are polarized oppositely to one another, the first and the second assemblies 52, 54 repel one another. The repelling forces press the distal assembly 52 against a distal stop 56 which is a collar of the endoscope shaft 4 in the represented exemplary embodiment. The proximal assembly 54 is pressed against a proximal stop 58. An air gap 60 remains, for example, between the distal central stator part pole shoe 48 and the proximal central stator part pole shoe 50.

Figure 7:
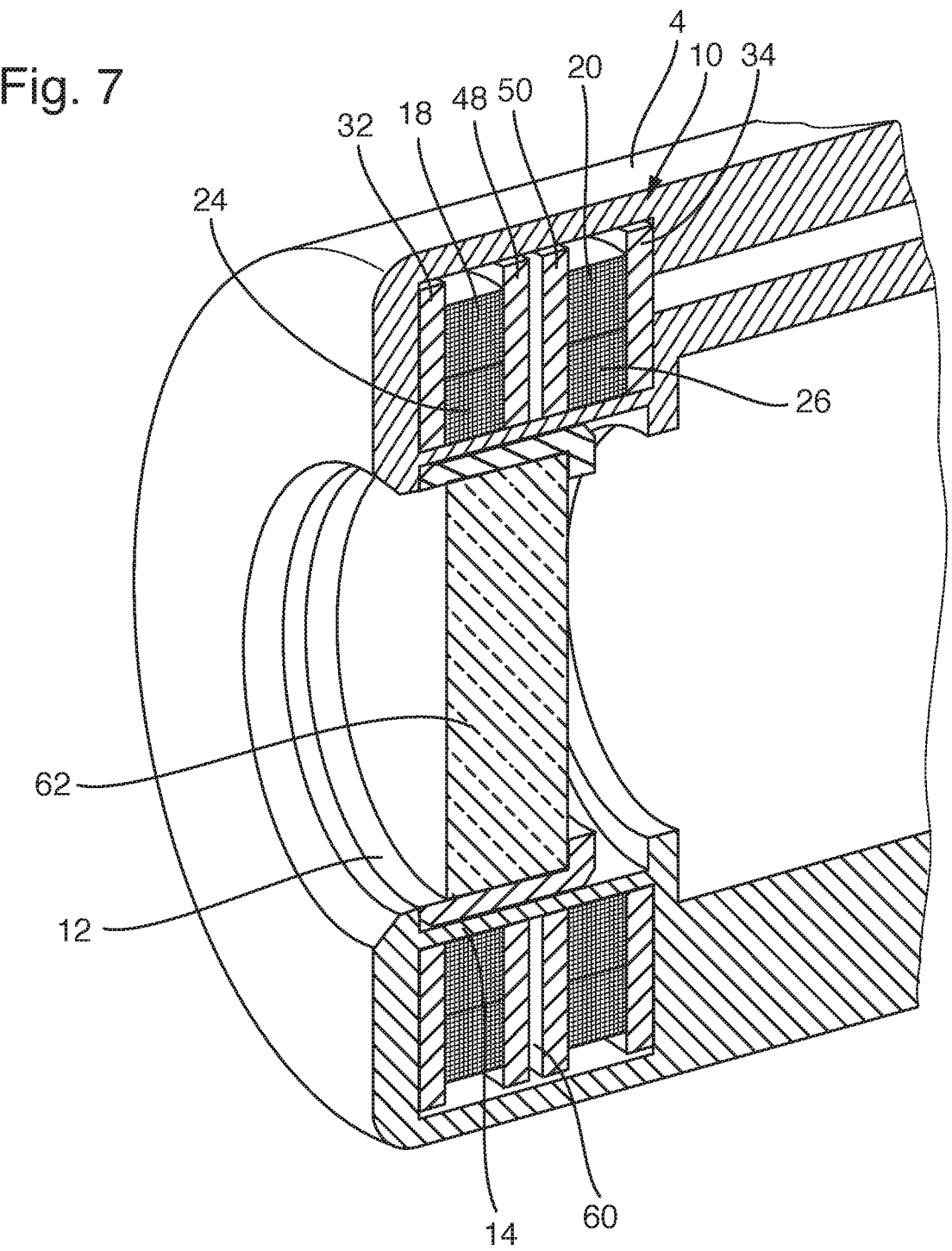
FIG. 7 illustrates said electromagnetic actuator installed in the endoscope tube in a schematically simplified perspective sectional view.

FIG. 7 shows the electromagnetic actuator 10 of FIG. 6 and installed in the endoscope shaft 4, in a schematically simplified perspective sectional view.

Figure 8:
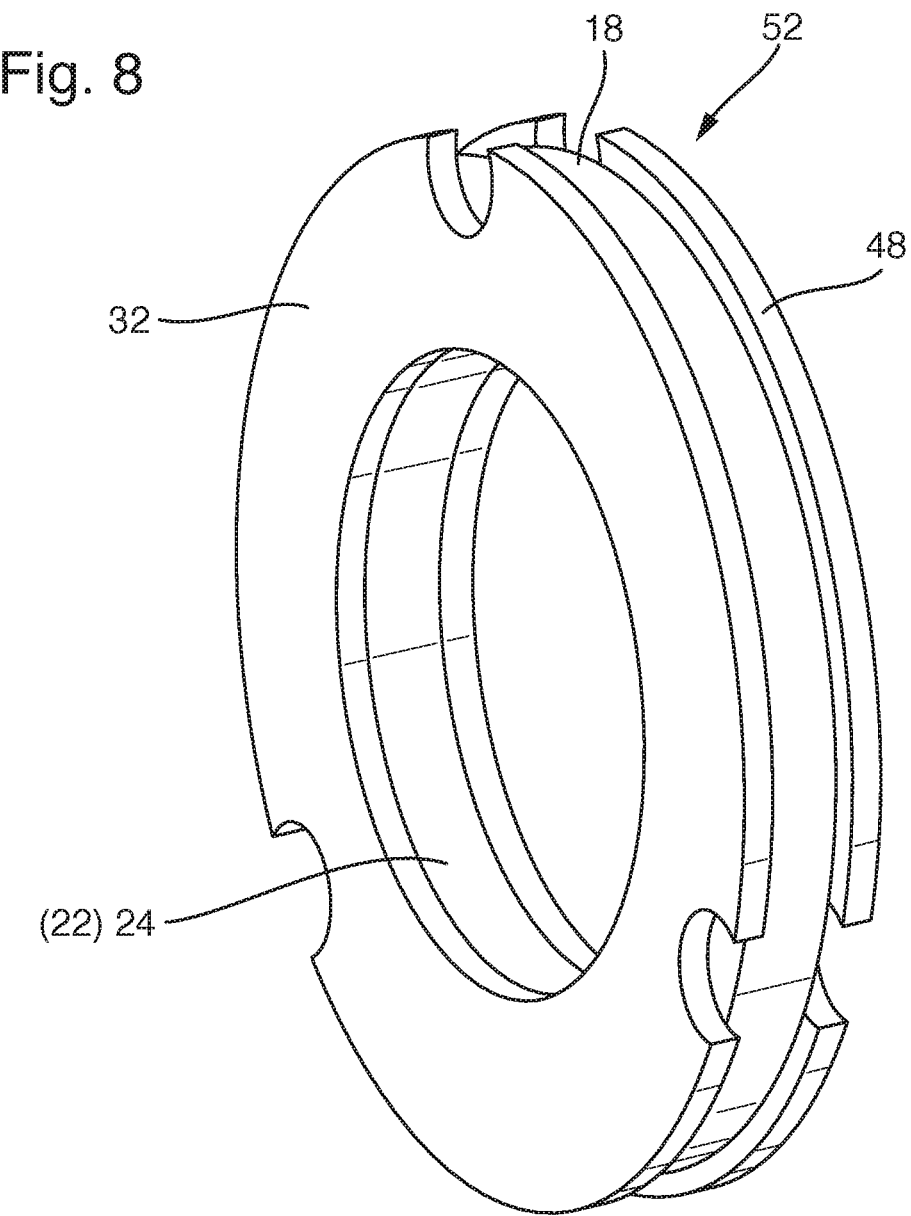
FIG. 8 illustrates a prefabricated assembly of the electromagnetic actuator in a schematically simplified perspective representation.

FIG. 8 shows a prefabricated assembly 52 (or 54), purely by way of example a proximal prefabricated assembly 54, in a simplified schematic and perspective representation.

Figure 9:
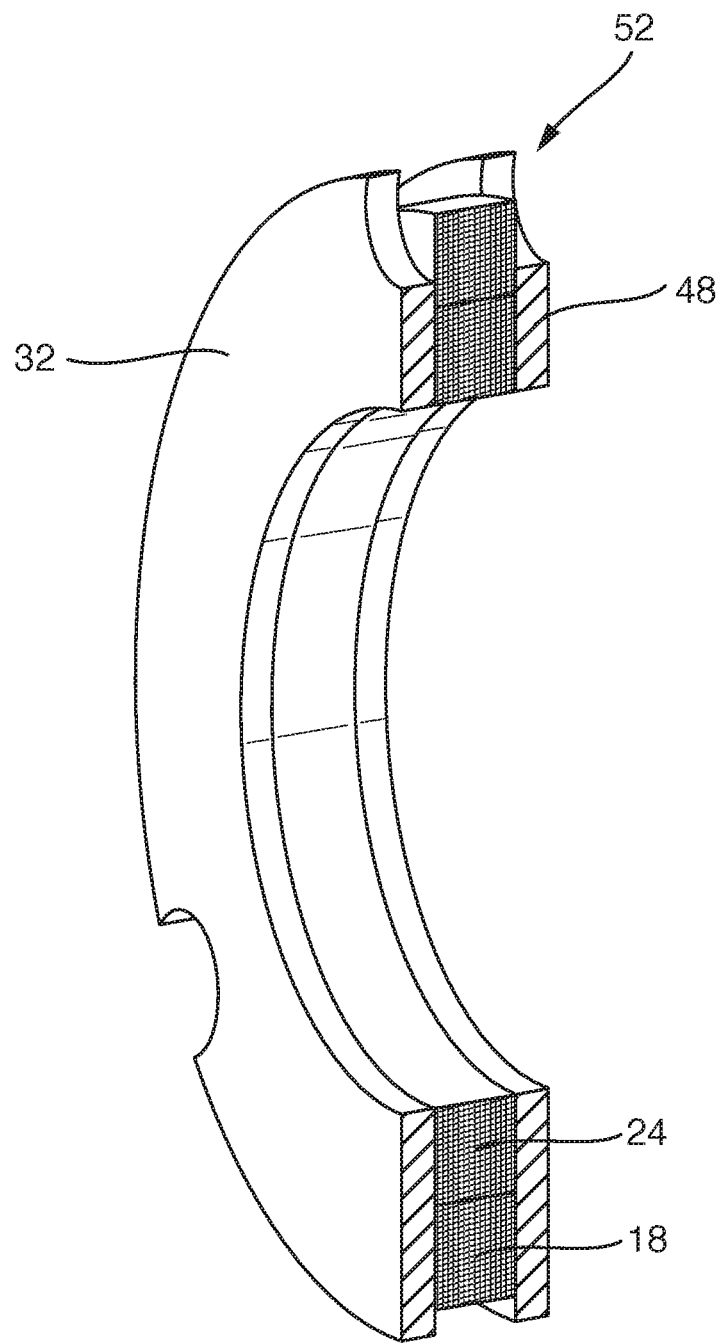
FIG. 9 illustrates said assembly in a sectioned schematically simplified perspective representation.

FIG. 9 shows said assembly 52 in a sectioned schematically simplified perspective representation.

In the represented exemplary embodiments of FIGS. 6 to 9, the permanent magnets 18, 20 are, purely by way of example, annular magnets. They enclose the coils 22 completely. For example, the permanent magnets 18, 20 are produced by embedding magnetically hard particles in a plastic matrix. An injection molding method is suitable for such production. In this way, it is advantageously possible to connect the components of the assemblies 52, 54 to one another and, at the same time, to produce the corresponding permanent magnet 18, 20 of the assembly 52, 54.

In order to contact the internal coils 22, according to a further exemplary embodiment, at least one of the connecting wires of the internal coil 22 is conducted through the permanent magnet 18, 20 produced on the basis of a plastic matrix.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Endoscope
4 Endoscope shaft
6 Distal end
8 Handle

10 Electromagnetic actuator
12 Rotor
14 Tube
16 Stator
18, 18' Distal permanent magnet
20, 20' Proximal permanent magnet
22 Coil
24 Distal coil
26 Proximal coil
28 Outer side of the coil
30 Outer side of the stator
32 Distal stator pole shoe
34 Proximal stator pole shoe
36 Central stator pole shoe
38 Inner side of the coil
40 Outer side of the permanent magnets
42 First static magnetic field
44 Second static magnetic field
46 Electromagnetic field
48 Distal central stator part pole shoe
50 Proximal central stator part pole shoe
52 Distal assembly
54 Proximal assembly
56 Distal stop
58 Proximal stop
60 Air gap
62 Lens
L Longitudinal axial direction
M Central longitudinal axis
R Radial direction

What is claimed is:

1. An electromagnetic actuator for use with a surgical instrument, the electromagnetic actuator comprising:
    a stator arranged outside a tube; and
    a rotor mounted in the tube such that the rotor can move in the tube in a longitudinal axial direction of the tube;
    the rotor comprises one or more of a paramagnetic and ferromagnetic material and is movable in the longitudinal axial direction by application of an electromagnetic field;
    the stator comprises:
    a distal permanent magnet and a proximal permanent magnet, the distal permanent magnet and the proximal permanent magnet being oppositely polarized in the longitudinal axial direction; and
        at least one electric coil for generating the electromagnetic field;
    wherein the distal permanent magnet and the proximal permanent magnet are arranged on an outer side of the coil facing away from the tube;
    a distal end of the stator is formed by a distal stator pole shoe and an opposite proximal end of the stator in the longitudinal axial direction is formed by a proximal stator pole shoe;
    the stator further comprises a central stator pole shoe arranged between the distal permanent magnet and the proximal permanent magnet in the longitudinal axial direction;
    the central stator pole shoe extends in a radial direction perpendicular to the longitudinal axial direction from an inner side of the coil facing the tube up to the outer side of the distal permanent magnet and the proximal permanent magnet facing away from the tube;
    the coil comprises a distal coil and a proximal coil, wherein the distal coil and the proximal coil extend in the longitudinal axial direction on both sides of the central stator pole shoe and are electrically connected to one another such that the distal coil generates a first magnetic field which is oriented identically to a second magnetic field generated by the proximal coil; and
    the central stator pole shoe is formed from a distal central stator part pole shoe and from a proximal central stator part pole shoe.

2. The electromagnetic actuator according to claim 1, wherein the distal permanent magnet and the proximal permanent magnet are configured to form a magnetic return element for the magnetic field generated by the electric coil.

3. The electromagnetic actuator according to claim 1, wherein an outer side of the distal permanent magnet and the proximal permanent magnet facing away from the tube forms at least one partial surface of an outer side of the stator facing away from the tube.

4. The electromagnetic actuator according to claim 1, wherein:
    the distal stator pole shoe, the distal coil, the distal permanent magnet and the distal central stator part pole shoe form a prefabricated distal assembly; and
    the proximal central stator part pole shoe, the proximal coil, the proximal permanent magnet and the proximal stator pole shoe form a prefabricated proximal assembly.

5. The electromagnetic actuator according to claim 4, wherein the distal stator pole shoe, the distal coil, the distal permanent magnet and the distal central stator part pole shoe of the distal assembly and/or the proximal central stator part pole shoe, the proximal coil, the proximal permanent magnet and the proximal stator pole shoe of the proximal assembly are bonded to one another.

6. The electromagnetic actuator according to claim 1, wherein at least one of the distal stator pole shoe, the central stator pole shoe and the proximal stator pole shoe extend in a radial direction perpendicular to the longitudinal axial direction from an inner side of the coil facing the tube up to an outer side of the distal permanent magnet and the proximal permanent magnet facing away from the tube.

7. The electromagnetic actuator according to claim 1, wherein the distal permanent magnet and the proximal permanent magnet are annular magnets which enclose the distal coil and the proximal coil.

8. The electromagnetic actuator according to claim 1, wherein the distal permanent magnet and the proximal permanent magnet are each formed from at least one bar magnet.

9. The electromagnetic actuator according to claim 8, wherein the distal permanent magnet and the proximal permanent magnet are each formed from multiple bar magnets, wherein the bar magnets forming the distal permanent magnet and/or the proximal permanent magnet are arranged uniformly spaced along a circumference of the tube.

10. The electromagnetic actuator according to claim 1, wherein at least one of the distal permanent magnet and the proximal permanent magnet comprise magnetically hard particles embedded in a plastic matrix.

11. A surgical instrument comprising:
    the tube; and
    the electromagnetic actuator according to claim 1.

12. The surgical instrument according to claim 11, wherein the tube is an insertion section of an endoscope.

* * * * *